(12) United States Patent
Hines et al.

(10) Patent No.: US 6,184,530 B1
(45) Date of Patent: Feb. 6, 2001

(54) ADJUSTABLE DUAL-DETECTOR IMAGE DATA ACQUISITION SYSTEM

(75) Inventors: Horace Hines, San Jose; Paul Hug, Saratoga; Mark L. Lamp, San Jose, all of CA (US)

(73) Assignee: ADAC Laboratories, Milpitas, CA (US)

(*) Notice: Under 35 U.S.C. 154(b), the term of this patent shall be extended for 0 days.

(21) Appl. No.: 07/704,759

(22) Filed: May 23, 1991

(51) Int. Cl.[7] .................................................. G01T 1/166
(52) U.S. Cl. ........................... 250/363.08; 250/363.04; 250/363.05; 250/363.1
(58) Field of Search ................... 250/363.05, 363.08, 250/363.1, 363.04; 378/209, 196

(56) References Cited

U.S. PATENT DOCUMENTS

| | | | |
|---|---|---|---|
| H12 | * 1/1986 | Bennett et al. | 250/363.04 |
| Re. 29,216 | 5/1977 | Colombo et al. | 250/363.08 |
| 3,011,057 | 11/1961 | Anger. | |
| 3,549,885 | 12/1970 | Andersson. | |
| 3,617,749 | 11/1971 | Massiot. | |
| 3,735,132 | 5/1973 | Carugati et al. | 250/363.08 |
| 3,756,549 | 9/1973 | Lange | 248/123 |
| 3,852,601 | 12/1974 | Casale | 250/363.08 |
| 3,870,886 | 3/1975 | Casale | 250/367 |
| 3,976,885 | 8/1976 | Brunnett et al. | 250/363.08 |
| 4,049,966 | 9/1977 | Luitwieler, Jr. | 250/366 |
| 4,057,727 | 11/1977 | Muehllehner et al. | 250/366 |
| 4,064,441 | 12/1977 | Casale | 250/363.08 |
| 4,216,381 | 8/1980 | Lange | 250/363 |
| 4,220,890 | * 9/1980 | Beekmans | 378/99 |
| 4,223,222 | 9/1980 | Gray et al. | 250/363 |
| 4,298,801 | * 11/1981 | Heitman et al. | 378/196 |
| 4,400,620 | * 8/1983 | Blum | 250/363.05 |
| 4,401,890 | 8/1983 | Blum | 250/363 S |
| 4,426,725 | * 1/1984 | Grady | 378/196 |
| 4,445,035 | 4/1984 | Ueyama | 250/363.04 |
| 4,476,389 | 10/1984 | Ueyama et al. | 250/363.05 |
| 4,503,331 | 3/1985 | Kovacs, Jr. et al. | 250/363 S |
| 4,613,122 | * 9/1986 | Manabe | 378/2.09 |
| 4,645,933 | * 2/1987 | Gambini et al. | 250/363.08 |
| 4,652,758 | * 3/1987 | Barfod | 250/363.05 |
| 4,652,759 | 3/1987 | Platz | 250/363.05 |

FOREIGN PATENT DOCUMENTS

| | | | |
|---|---|---|---|
| 3145430A1 | 5/1983 | (DE) | G01T/1/29 |
| 0332937A1 | 1/1989 | (EP). | |
| 0465952A2 | 1/1992 | (EP). | |
| 1572809 | 12/1976 | (GB). | |
| 2120060 | 11/1983 | (GB). | |

OTHER PUBLICATIONS

Performance Analysis of Three Camera Configurations for Single Photon Emission Computed Tomography, Lim, et al, *IEEE Transactions on Nuclear Science*, vol. NS–27, No. 1, Feb. 1980.

A New Development in Single Gamma Transaxial Tomography Union Carbide Focused Collimator Scanner, Stoddart, et al., *IEEE Transactions on Nuclear Science*, Apr. 1979, pp. 2710–2712

(List continued on next page.)

Primary Examiner—Constantine Hannaher
(74) Attorney, Agent, or Firm—Blakely, Sokoloff, Taylor & Zafman, LLP

(57) ABSTRACT

The imaging system has two detectors which can be rotated in a circular path about an object with the angular displacement between the detectors and their radial position with respect to the axis being adjustable. Preferably, the distance of the detectors from the lateral axis is adjustable to increase resolution of the system. A gantry has supports for drive gear rings for the detectors with radial motion mechanisms connecting one detector to the interior surface of a drive gear ring and the other to the exterior of its drive gear ring via a support arm. A drive gear and idler gear move one detector along the circular path and a radial drive motor moves the detectors radially with respect to the axis.

11 Claims, 8 Drawing Sheets

OTHER PUBLICATIONS

Physical Factors Affecting Quantitive Measurements Using Camera–Based Single Photon Emission Computed Topagraphy (SPECT), Jasczak, et al, *IEEE Transactions on Nuclear Science*, Feb. 1981, pp. 69–80.

Effect of an Elliptical Orbit on Spect Resolutions and Image Uniformity, Gottschalk, et al, Proceedings of Third World Conference of Nuclear Energy and Medicine, Aug. 29–Sep. 2, 1982, in *Nuclear Medicine and Biology*, edited by C. Raynaud, Pergamon Press, France, 1982, pp. 1026–1029.

The Current Status of Tomographic Scanning, Kuhl, *Fundamental Problems in Scanning*, edited by Gottschalk, et al, Charles C. Thomas. Publisher, Springfield, Illinois, 1968, pp. 179–190.

Spect Resolution and Uniformity Improvements by Noncircular Orbit, Gottschalk, et al, *Journal of Nuclear Medicine*, 1983, pp. 822–828.

"Principles of Instrumentation in Spect," Robert Eisner, Journal of Nuclear Medicine, vol. 13, #1, Mar. 1985 pp 23–31.

"Computed Tomography in Nuclear Medicine," John Keyes, (Chapter IN) Computer Methods, C.V. Mosley, 1977, pp. 130–138.

"Single Photon Emission Computed Tomography" Bernard Oppenheim et al, (Chapter IN) Effective Use of Computers in Nuclear Medicine, Geifand et al, McGraw–Hill, 1988 pp. 31–74.

"Collimater Selection for Spect Brain Imaging: The Advantage of High Resolution," Stefan P. Mueller et al, Journal of Nuc. Med., vol. 27, #11, Nov. 1986 pp. 1729–1738.

"Dual–Head Genesys," Adac Lab. Product Bulletin, ADAC Labs., Milpitas, CA, undated.

"Genesys," ADAC Lab. Product Bulletin, ADAC Laboratories, Milpitas, CA, undated.

* cited by examiner

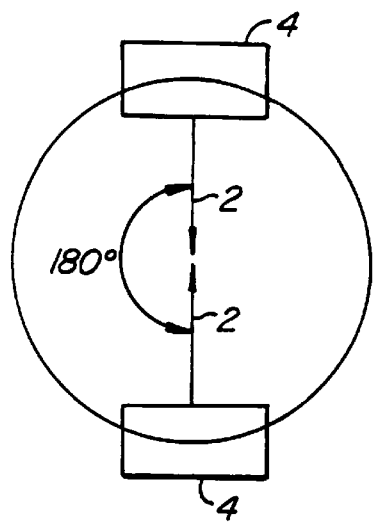
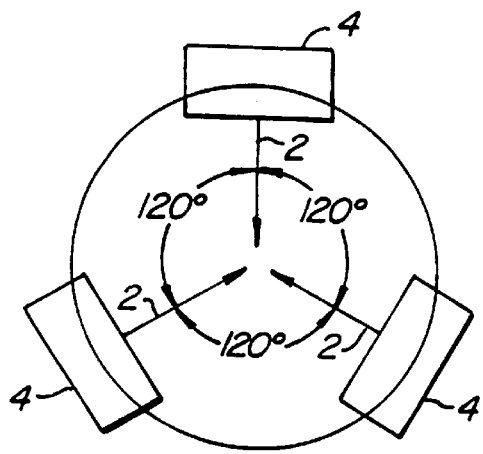
FIG. 1A. PRIOR ART
FIG. 1B. PRIOR ART
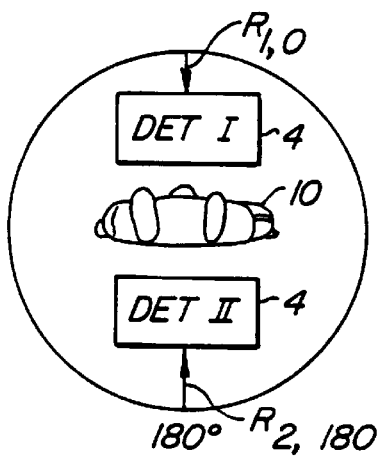
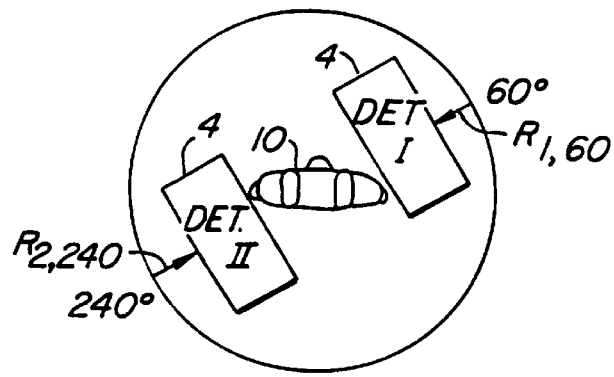
FIG. 1C. PRIOR ART
FIG. 1D. PRIOR ART
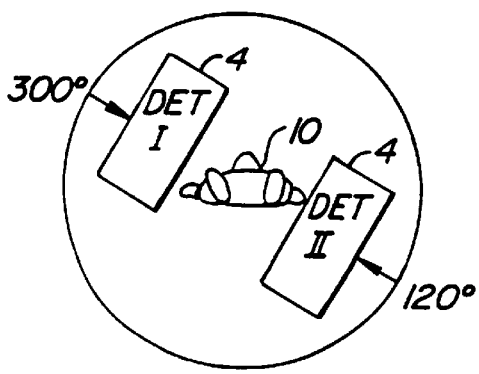
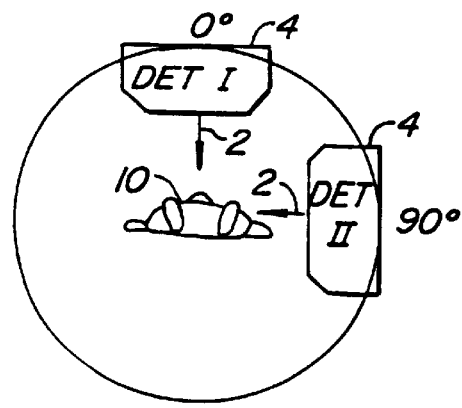
FIG. 1E. PRIOR ART
FIG. 2A.

ADJUSTABLE DUAL-DETECTOR IMAGE DATA ACQUISITION SYSTEM

BACKGROUND OF THE INVENTION

1. Field of the Invention

The present invention relates generally to imaging systems and more particularly to imaging systems for use in nuclear medicine.

2. Description of the Relevant Art

Gamma ray cameras are used in nuclear medicine to generate high quality images for brain, SPECT (Single Photon Emission Computer Tomograph), and total body bone studies. These cameras are most frequently used for cardiac and total body bone studies.

It is very important that the gamma ray camera be designed for high patient throughput for both economic and therapeutic reasons. The cost for diagnosing each patient is reduced if more patients can be diagnosed per unit time. For very sick patients or patients in intensive care it is important to minimize the time required to acquire image data. Patient throughput is increased if imaging time is reduced. Other factors, such as patient set-up time also affect patient throughput.

Modern gamma ray cameras utilize detectors, such as Anger cameras, having a wide field of view so that it is possible to image the full width of the body of a patient at each angular stop without the requirement of rectilinear scanning. These detectors use thick lead collimators to focus images and are thus very heavy. The collimators must be positioned as close to the patient as possible to acquire image data required to generate high resolution images. The image data acquired by the detectors is processed by a computer to generate an image. Techniques for processing image data are well-know in the art and described in "Principles of Instrumentation in SPECT" by Robert Eisner, *Journal of Nuclear Medicine,* Vol. 13, #1, March 1985, pp. 23–31; Computed Tomography in Nuclear Medicine" by John Keyes, (chapter in) *Computer Methods,* C. V. Mosley, St. Louis, 1977, pp. 130–138; and "Single Photon Emission Computed Tomography," by Bernard Oppenheim and Robert Appledown, (chapter in) *Effective Use of Computers in Nuclear Medicine,* Michael Gelfand and Stephen Thomas, McGraw-Hill Book Co., New York 1988, pp. 31–74.

Recent technological innovations have produced dual-head systems, with two detectors having their detector image direction arrows oriented at a fixed angle of 180°, and triple-head systems, with three detectors having their image direction arrows oriented at fixed angles of 120°, SPECT gamma ray cameras capable of rapid, high quality SPECT imaging. FIGS. 1A and 1B are schematic diagrams depicting the fixed orientation of the detector image direction arrows 2 of the detectors 4 in a dual-head and triple-head system.

When the detectors rotate about the patient, a lateral axis is defined as the mechanical axis of rotation aligned with the computer matrix for reconstructing the SPECT images.

The single, dual, and triple head cameras each have certain features which are advantageous for a particular type of application. To determine which system is best for a particular application factors such as 1) the ability of the camera to perform required imaging tasks; 2) the quality of the images generated; and 3) patient throughput should be considered.

The acquisition of data for a total body scan requires movement of the detector along the length of the patient's body. The dual-head system is very efficient because image data for anterior/posterior images can be acquired simultaneously. The time required to complete a scan can be reduced from 45 to 60 minutes, for a single-head camera, to 30 minutes. The triple-head system is no more efficient than the single-head system because the detectors cannot be aligned to acquire simultaneous anterior/posterior or left/right lateral data.

To generate high-quality SPECT for brain, bone, or liver studies views taken along a complete 360° circle (360° scan) around the body of the patient are required. Typically, about 64 to 128 angular stops are required to acquire the image data. The above-described dual-head camera reduces the imaging time to ½ the imaging time of a single-head system because data is acquired from two stops simultaneously. The triple-head camera reduces the imaging time to about ⅓ the imaging time of a single-head system because data is acquired from three stops simultaneously.

For cardiac SPECT studies, the analysis of complex imaging considerations has led to the use of at least 32 stops over a 180° arc about the patient's body (180° scan). For a 180° scan the imaging time of a single-head and dual-head system are the same because only one detector of the dual-head system is within the 180° arc at any given time. A triple-head system reduces the image time to about ⅔ the time of a single-head system for a 180° scan because two detectors are within the 180° arc about ⅓ of the time.

In view of the above it is apparent that the mechanical system for orienting the detectors must be designed to provide a mechanism for accurately orienting the detectors at various angular stops relative to the patient and to position the collimator as close to the patient as possible. Additionally, the system must be stable so that the heavy detectors are held still at each stop to facilitate the acquisition of accurate imaging data. Other attributes that are required of the mechanical system are ease of patient positioning, size of footprint, and overall size.

Further, as described above, the existing systems each have advantages for particular applications but generally lack the flexibility for optimal performance over a range of applications. Additionally, although cardiac SPECT imaging accounts for about 33% of the use of gamma ray cameras, none of the systems significantly reduce the imaging time for the 180° scan used in forming cardiac SPECT images.

SUMMARY OF THE INVENTION

The present invention is a unique system for reducing the imaging time required to generate a 180° SPECT image. According to one aspect of the invention, first and second detectors are positioned with a relative angle of 90° to reduce the imaging time for a 180° scan by a factor of two over a two detector systems having the detectors positioned at a fixed relative angle of 180°.

According to another aspect of the invention, the angular displacement between two detectors may adjusted to any angle between about 90° and 180° and the detectors can be rotated to any desired angular position along a circular path centered on a lateral axis. Thus, the system can be optimally configured for total body scans and 360° SPECT (relative angular displacement of 180°) and 180° SPECT (relative angular displacement of 90°) to provide a very flexible system.

According to further aspect of the invention, each detector can be independently rotated along different circular paths centered on the lateral axis.

According to a still further aspect of the invention, each detector may be independently moved toward or away from the lateral axis.

According to a still further aspect of the invention, extended collimators are used to decrease the distance between the collimator and the body of a patient when the relative angular displacement of the detectors is less than 180° to improve resolution.

According to a still further aspect of the invention, a detector used to form a lateral image of a patient is narrower than the detector used to form a horizontal image so that the detectors can be positioned nearer to the body of a patient to improve resolution.

According to a still further aspect of the invention, a table, oriented parallel to the lateral axis for supporting a patient, is displaced vertically and horizontally from the lateral axis to move the body of the patient close to the detectors to improve resolution.

Other features and advantages of the invention will be apparent in view of the appended figures and following detailed description.

BRIEF DESCRIPTION OF THE DRAWINGS

FIGS. 1A and 1B are schematic views depicting the fixed orientation of the detectors for existing dual-head and triple head imaging systems;

FIGS. 1C–1E are schematic views showing 3 of the multiple angular stops required for a 360° scan with the angular displacement of the detectors at 180°;

FIGS. 2A–2C are schematic views showing 3 of the multiple angular stops required for a 180° scan with the angular displacement of the detectors at 90°;

DESCRIPTION OF THE PREFERRED EMBODIMENT

FIGS. 1C–1E depict the required angular stops for two detectors 4 displaced by 180° to accomplish a 360° scan. In the 180° configuration the size of the detectors does not limit their radial motion and the detectors 4 can be positioned to touch the body 10 of the patient at each stop. However, the detectors cannot be moved in circular path while maintaining close proximity to the body of the patient 10 because the body 10 of the patient is not circular.

Figure 2B:
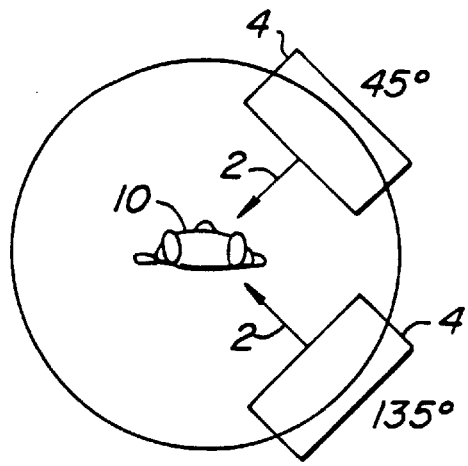
Figure 2C:
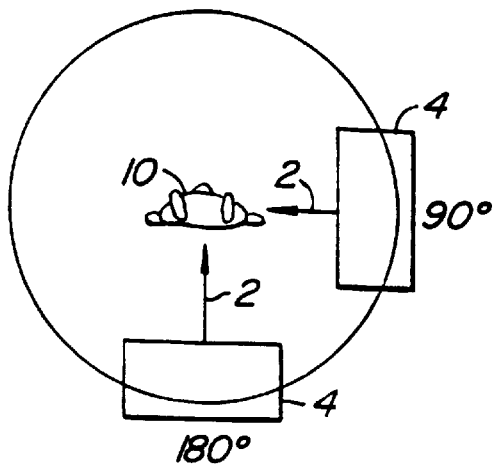

FIGS. 2A–2C depict a preferred embodiment of the invention. The detectors 4 have their image direction arrows oriented at 90° to reduce the imaging time of a 180° scan to ½ the imaging time of a single-head system because data is acquired from two stops simultaneously.

Figure 3:
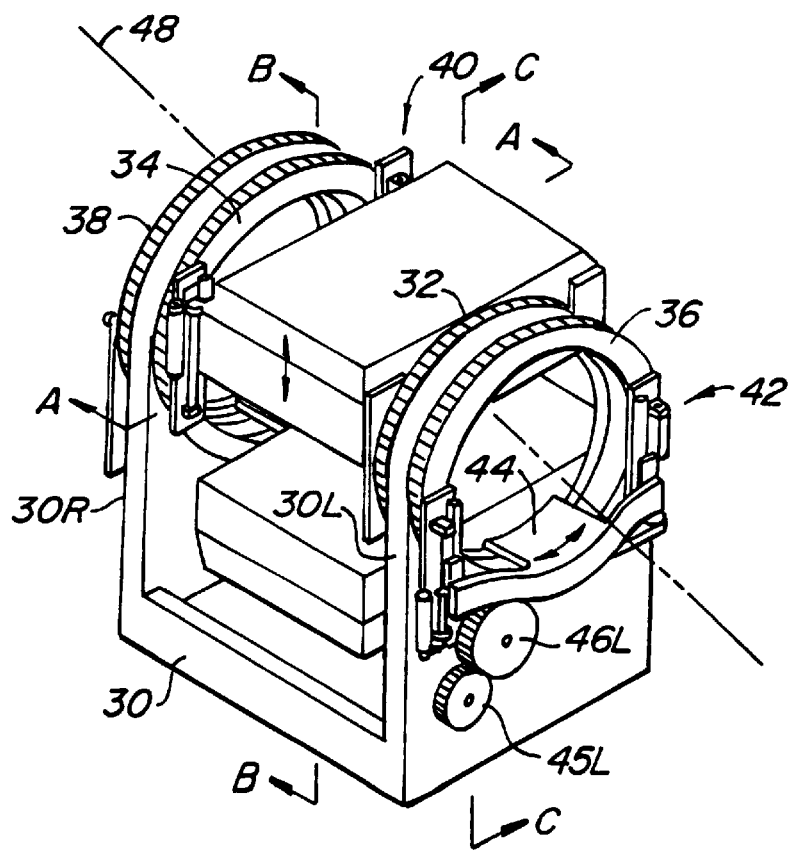
FIG. 3 is a perspective view of a preferred embodiment of the invention.

FIG. 3 is a perspective view of a preferred embodiment of the invention that allows the adjustment of the relative angular displacement of the detectors to have any magnitude from less than 90° upto 180°. Further, each detector may be independently moved toward or away from the lateral axis 48.

In FIG. 3, a gantry 30, having left and right upright sections 30L and 30R, supports first and second detector I drive gear rings 32 and 34 and first and second detector II drive gear rings 36 and 38. A detector I radial motion mechanism 40 connects detector I to the interior surface of the second detector I drive gear ring 34 and a detector II radial motion mechanism 42 connects detector II, via a first detector II support arm 44, to the exterior surface of the first detector II drive gear ring 36.

A left drive gear 45L and idler gear 46L controllably engages the first detector drive gear ring 36 to move detector II in a circular path about a lateral axis 48.

Figure 4:
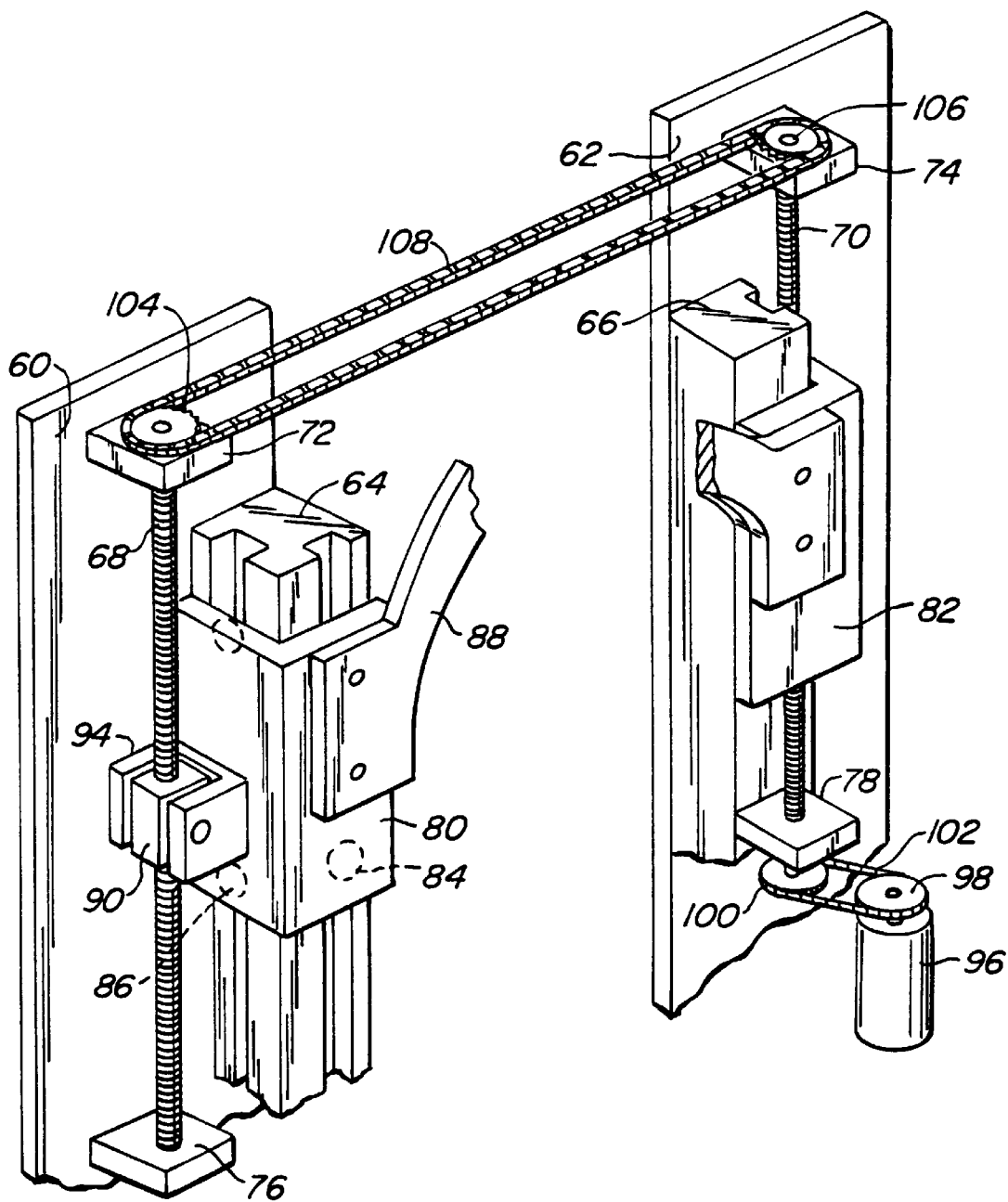
FIG. 4 is a view taken along A—A of FIG. 3.

FIG. 4 is perspective view of the detector I radial motion mechanism 40 taken along A—A of FIG. 3. In FIG. 4, base plates 60 and 62 having slotted guide bars 64 and 66 fixedly mounted thereon, are attached to the interior surface of the second detector I ring gear 34. Lead screws 68 and 70 are rotatably mounted in bearing blocks 72, 74, 76, and 78 which are fixedly attached to the base plates 60 and 62. Arm supports 80 and 82 are engaged with the grooves of the guide bars 64 and 66 by guide rollers 84 and 86. Swivel nuts (only one 90 is shown) couple the lead screws to the arm supports 80 and 82 via brackets (only one 94 is shown). A detector support arm 88 is fixedly mounted to the arm supports 80 and 82.

A drive motor has a lead drive gear 98 coupled to a trailer gear 100 mounted on the second lead screw 70 by a drive chain 102. First and second lead screw coupling gears 104 and 106 are coupled by a coupling chain 108.

Figure 5:
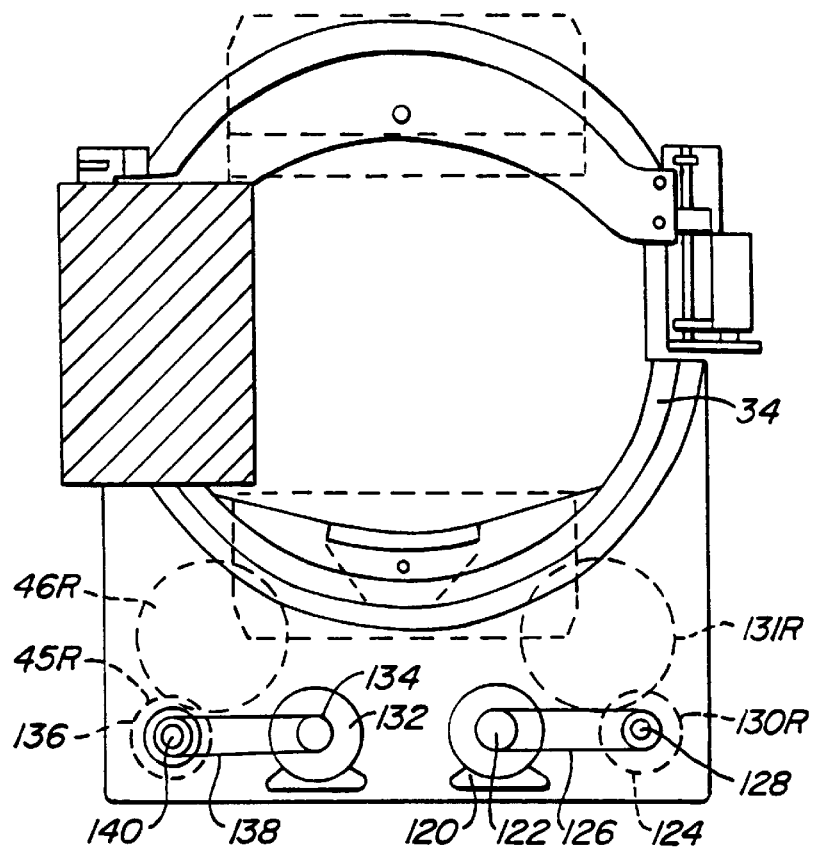
FIG. 5 is a view taken along B—B of FIG. 3.

FIG. 5 is an end view, taken along 5—5 of FIG. 3, of the rotary drive mechanisms for detectors I and II. In FIG. 5, a first rotary drive motor 120 has a lead drive pulley 122 coupled to a transmission shaft drive pulley 124 by a first drive belt 126. A first transmission shaft 128 is coupled to the second detector I ring gear 34 by a right drive gear 130R and idler gear 131R. The first transmission shaft extends through the gantry 30 parallel to the lateral axis 48 and is also coupled to the first detector I ring gear 32 by left drive and idler gears 130L and 131L (not shown). The drive and idler gears 130 and 131 for driving the detector I ring gears 32 and 34 are located on the interior sides of the upright sections 30L and 3OR of the gantry 30.

Similarly, a second rotary drive motor 132 has a lead drive pulley 134 coupled to a transmission shaft drive pulley 136 by a second drive belt 138. A second transmission shaft 140 is coupled to the second detector II ring gear 38 by a right drive gear 45R and idler gear 46R (depicted in phantom). The second transmission shaft extends through the gantry 30 parallel to the lateral axis 48 and is also coupled to the second detector II ring gear 36 by drive and idler gears. The drive and idler gears 45 and 46 for driving the detector II ring gears 36 and 38 are located on the exterior sides of the upright sections 30L and 30R of the gantry 30.

Figure 6:
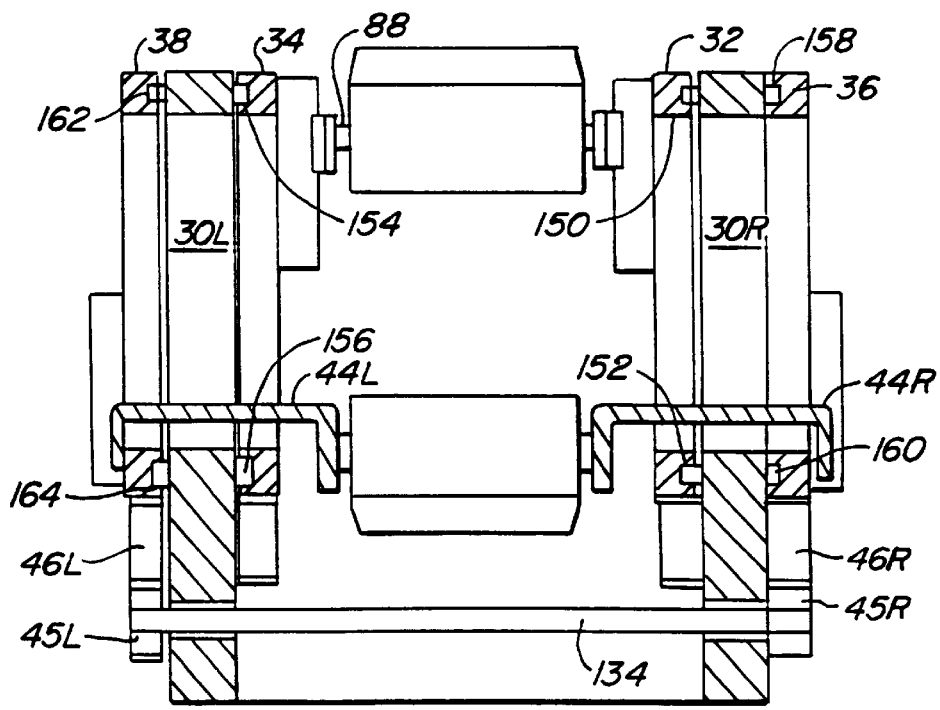
FIG. 6 is a view taken along C—C of FIG. 3.

FIG. 6 is a cross-sectional view, taken along 6—6 of FIG. 3, depicting the drive and detector support mechanisms. The detector ring gears 32, 34, 36, and 38 have support grooves which are engaged with gear support bearings 150, 152, 154, 156, 158, 160, 162, and 164 mounted on the upright sections 30L and 3OR of the gantry 30. Detector I and the detector I radial drive mechanism are mounted on the interior surfaces of the first and second detector I ring gears 32 and 34. The radial drive mechanism for detector II is mounted on the exterior surface of the detector II ring gears 36 and 38. The detector II support arms 44R and L are coupled to the exterior surfaces of the detector II ring gears and extend through the annular space created by the ring gears and supports detector II.

Figure 7:
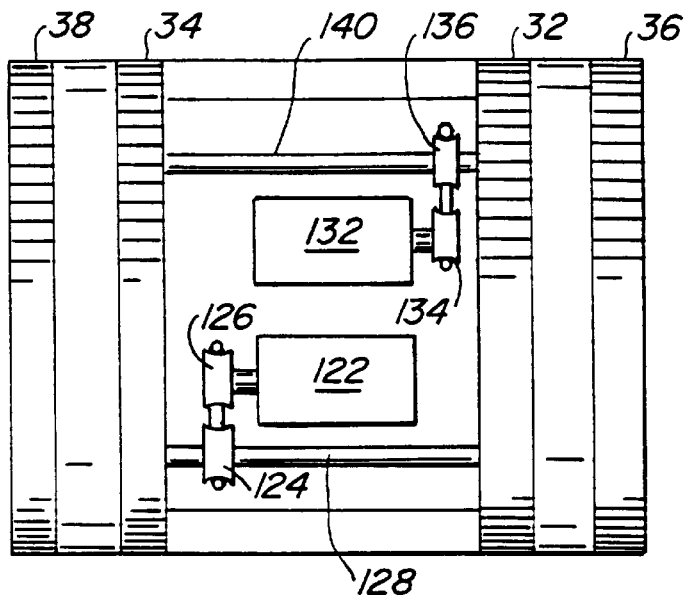
FIG. 7 is a top view of the embodiment depicted in FIG. 3.

FIG. 7 is a top view of the embodiment depicted in FIG. 3 and further depicts the details of the rotary drive mechanism. The first transmission shaft 128 transmits the rotary motion of the first rotary drive motor 122 to both the first and second detector I ring gears 32 and 34 and the second transmission shaft 140 transmits the rotatory motion of the second rotary drive motor 132 to the first and second detector II ring gears 36 and 38.

The operation of the embodiment depicted in FIGS. 3–7 will now be described. Detectors I and II may be independently rotated about the lateral axis 48 by activating either the first or second rotary drive motors 132 or 122. If the first rotary motor is activated rotary motion is transmitted to the first detector ring gears 32 and 34 which in turn impart rotary motion to detector I through the support arms 88.

Additionally, each detector may be independently moved radially toward or away from the lateral axis 48 by activating the radial drive motor 96 in the radial drive mechanism for the detector.

Figure 7A:
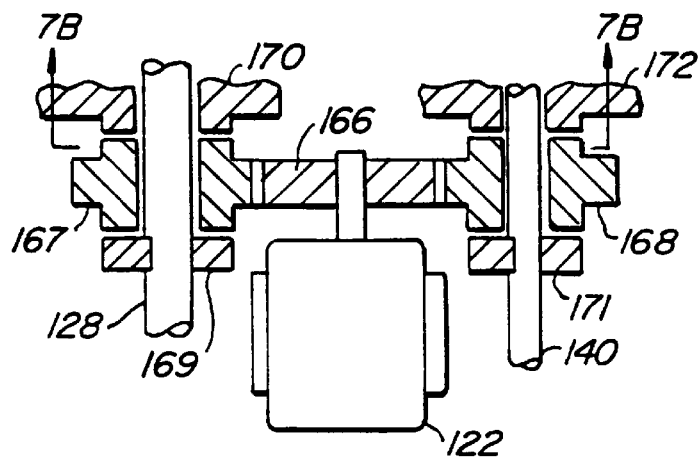
FIGS. 7A–7C are a schematic views of an alternative rotational drive mechanism.
Figure 7B:
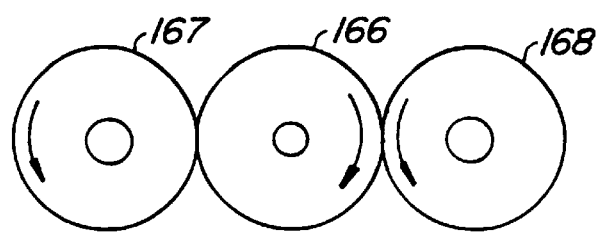

FIGS. 7A and 7B depict an alternative rotary drive mechanism utilizing a single rotary drive motor 122 coupled to the first and second transmission shafts 128 and 140. In FIG. 7A a lead drive gear 166 is directly coupled to the shaft drive gears 167 and 168 to move to rotate both transmission shafts 128 and 140 in the same direction.

The rotational motion of shaft drive gear 166 is transmitted to the first transmission shaft 128 when a first electromagnetic clutch 169 is engaged and rotation of the first transmission shaft 128 is stopped when a first electromagnetic brake 170 is engaged. Similarly, the rotational motion of shaft drive gear 166 is transmitted to the second transmission shaft 140 when a second electromagnetic clutch 171 is engaged and rotation of the second transmission shaft 140 is stopped when a second electromagnetic brake 172 is engaged.

FIG. 7B is a view, taken along A—A of FIG. 7A, depicting the rotation of the lead gear 166 and shaft drive gears 167 and 168.

In operation, both detectors I and II are rotated when both clutches 169 and 171 are engaged and both brakes 170 and 172 are disengaged. Detector I is moved independently if the first clutch 169 is engaged and the first brake 170 is disengaged and detector II is moved independently if the second clutch 171 is engaged and the second brake 172 is disengaged. The brakes are used for safety reasons and to counteract the system in balance.

Figure 7C:
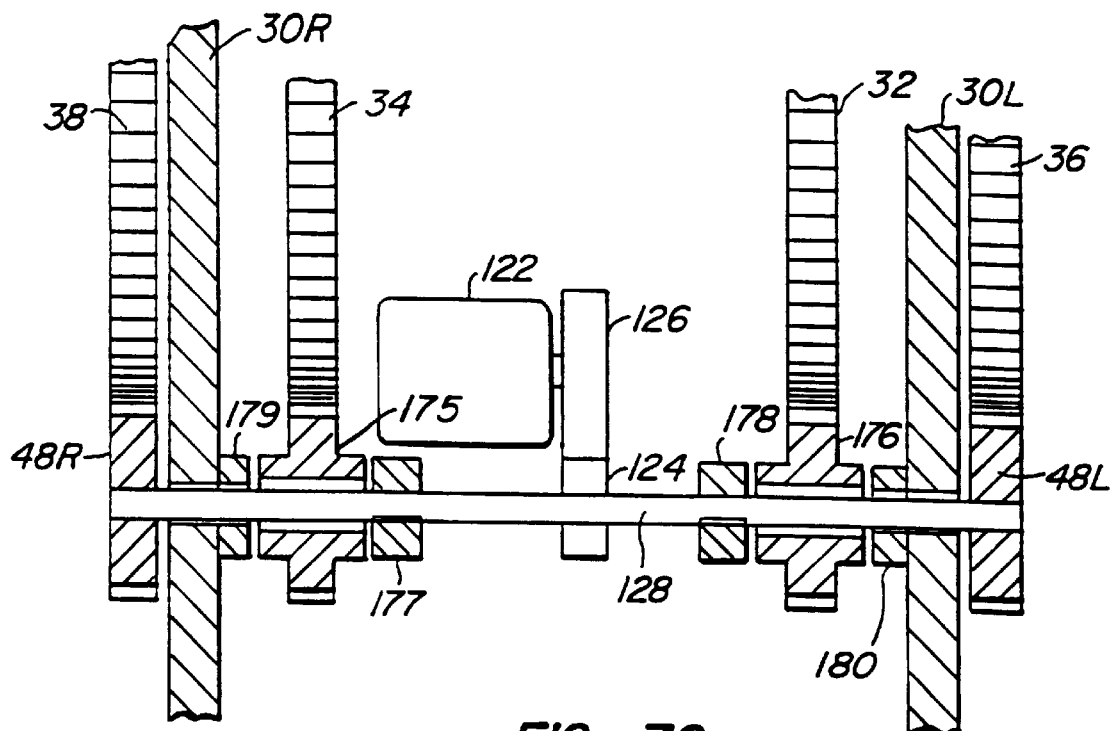

FIG. 7C is a schematic view of an alternative drive system that uses a single drive motor 122 and drive shaft 128. Drive gears 48 are fixed on the end of the shaft 128 and engaged with the first and second detector II ring gears 36 and 38. First and second shaft gears 175 and 176 couple the rotational motion of the shaft 128 to the first and second detector I ring gears 34 and 32 when electromagnetic clutches 177 and 178 are engaged. The motion of the first and second detector I ring gears 32 and 34 is stopped when the electromagnetic brakes 179 and 180 are disengaged.

In operation, both detectors rotate together when both clutches 177 and 178 are released and the brakes 179 and 180 are released and the rotational drive motor 122 is activated. Detector II is independently rotated to adjust the angular displacement relative to detector I when the brakes 179 and 180 are engaged and the clutches 177 and 178 are engaged.

Figure 8:
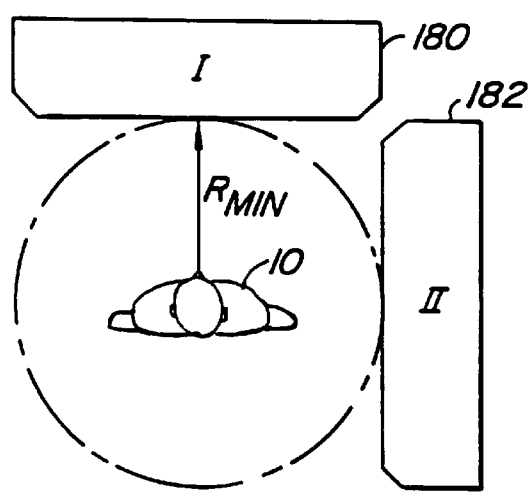
FIG. 8 is a schematic view of two detectors oriented at 90°.

As described above, high patient throughput requires that detectors having a wide field of view be utilized. However, when the detector image direction arrows 2 are oriented at 90°, to efficiently perform a 180° scan, the physical size of the detectors 4 limits their radial motion. Referring to FIG. 8, the detector edges will touch when the radius Rmin is reached. Thus the detectors 4 are not able to touch the body 10 of the patient which is necessary to achieve high resolution. Also, each detectors I and II has a lateral shielding section 182 to prevent external gamma rays from reaching the scintillation medium.

Figure 9:
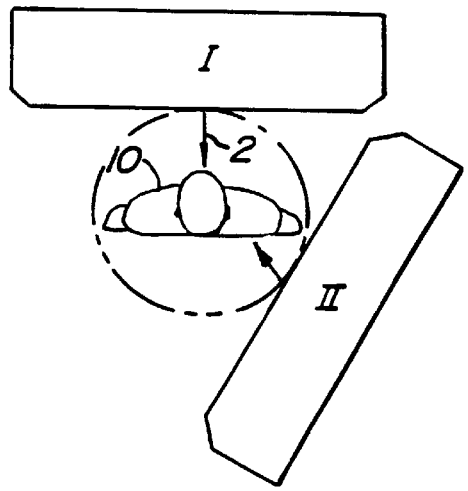
FIG. 9 is a schematic view of two detectors oriented at 120°.

In one embodiment of the invention the detector image direction arrows 2 are oriented at 120° when a 180° scan is to be performed. As depicted in FIG. 9, this orientation allows greater radial motion to allow the detectors I and II to be positioned closer to the body 10 of the patient than in the 90° configuration. However, the imaging time is reduced to only about ⅔ of the imaging time of a single-head system because both detectors I and II are within the 180° arc only a fraction of the time.

Figure 10:
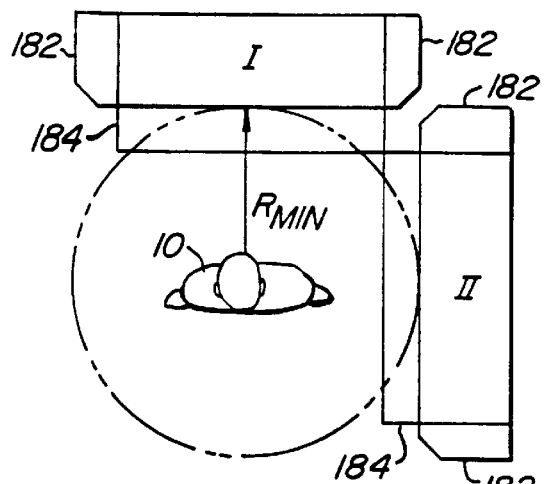
FIG. 10 is a schematic view of two detectors having extended collimators and oriented at 90°.

In another embodiment, depicted in FIG. 10, extended collimators 184 are utilized to decrease Rmin and to place the collimator 184 closer to the body 10 of the patient.

Additionally, as depicted in FIG. 10, the detectors I and II have bevelled edges that allow the detectors to be moved closer together when oriented at 90° thereby reducing $R_{MIN}$.

Figure 10A:
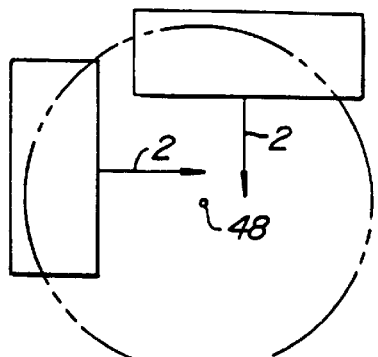
FIG. 10A is a schematic view of two detectors having their centers displaced from the lateral axis.

In FIG. 10A, a configuration where the centers of the detectors I and II are displaced from the lateral axis 48 so that the image arrows 2 do not point toward the lateral axis is depicted. SPECT algorithms for correcting for such displacements are known in the art.

Figure 11:
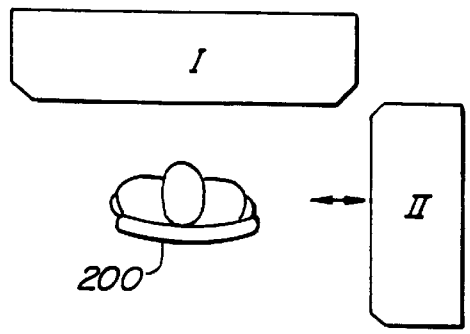
FIG. 11 is a schematic view of two detectors oriented at 90° with a reduced lateral detector.

Alternatively, as depicted in FIG. 11, detector II is oriented laterally to the body 10 of the patient and has a narrower cross-section and field of view. The smaller cross-section of detector II facilitates closer positioning of the collimator to the body of the patient.

Figure 12:
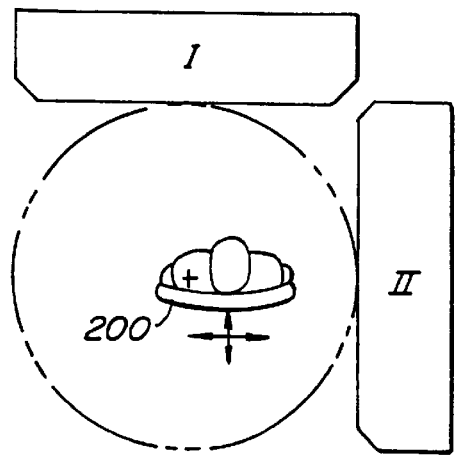
FIG. 12 is a schematic view depicting a patient table that can be horizontally and vertically displaced relative to the lateral axis.

In another embodiment of the invention, depicted in FIG. 12, a table 200 holding the patient is displaced vertically and horizontally from the lateral axis 48 so that the body 10 of the patient touches the detectors I and II.

Figures 13A, 13B:
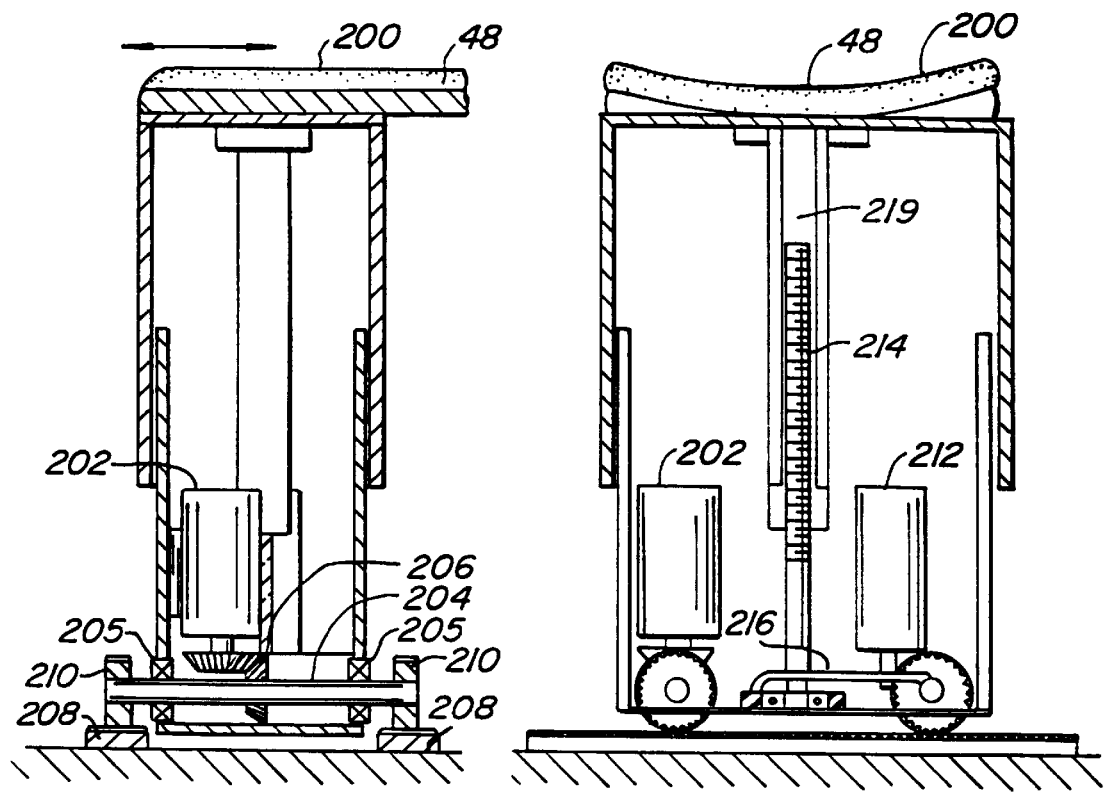
FIGS. 13A and 13B are cut away views of mechanisms for displacing the table from the lateral axis.

FIGS. 13A and B depict mechanisms for imparting horizontal motion and vertical motion of the table 200 relative to the lateral axis 48. In FIG. 13A, a view taken parallel to the lateral axis 48, a horizontal drive motor 202 imparts rotary motion to an axle 204, supported by bearings 205, through bevel gear 206. Horizontal motion of the table 200 is effected by movement along gear racks 208, oriented perpendicularly to the lateral axis 48, through rotational motion imparted to gears 210 engaged to gear racks 208 by axle 204.

In FIG. 13b, a view taken perpendicular to the lateral axis 48, a vertical drive motor 212 imparts rotational motion to a lead screw 214 through a drive mechanism 216. The threads of the lead screw 214 are engaged to threads of a telescope tube 219 to impart vertical motion to the telescope tube and table 200 when the vertical drive motor 212 is activated.

Figure 14:
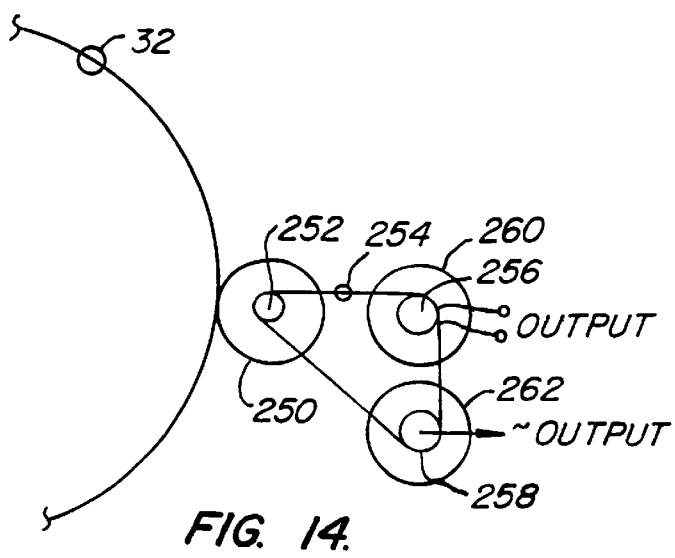
FIG. 14 is a schematic view of a positional feedback mechanism.

FIG. 14 depicts a positional feedback device for indicating the positions of the detectors. In FIG. 14, a sensor gear 250 engages a ring gear 32 and has a sprocket 252 coupled to a chain 254. The chain engages sprockets 256 and 258 coupled to a potentiometer 260 and an encoder 262.

In operation, the potentiometer 260 is used for coarsely indicating position and the encoder 262 for finely indicating position. For example, the sprockets can be sized so that for each revolution of the ring gear 32 the potentiometer 260 makes 10 turns varying the resistance from 0 to 1,000 ohms. If power is lost the potentiometer 260 will not loose its position.

Similar devices are utilized to indicate the radial position of the detectors and the vertical and horizontal displacement of the table 200.

An improved method for imaging that utilizes the movable table 200 will now be described. The table is moved up and down or left and right using microprocessor control and the positional feedback device enables the microprocessor to calculate the position of the table.

First, the motion limits of the detectors and table are defined. The operator moves the detectors to have the desired relative angular displacement (e.g., 90°). The table holding the patient is positioned on the lateral axis. The operator then moves the detectors into the desired position relative to the patient (e.g. anterior and lateral). The operator then moves the table so that the body of the patient touches the lateral detector and the microprocessor stores the x-location. The operator the moves the table so that the body of the patient touches the anterior detector and the microprocessor stores the y-location. The microprocessor then calculates the required table motion based on the size of the detectors, the number of angular stops required, and x and y locations determined above.

Once the motion limits are defined image data is acquired. The table is moved to a location to allow motion of the detectors and the detectors are moved to the first angular stop. The table is then moved to the starting position for the first angular stop and data is acquired. The positions of the table and the detectors are stored. The procedure is repeated until data is acquired for all the required angular stops. The stored location data is utilized to generate an image from the acquired data.

The invention has now been described with reference to the preferred embodiments. Alternatives and substitutions will now be apparent to persons of ordinary skill in the art. For example, if detectors I and II were to be maintained at a fixed angle, e.g., 120° or 90°, then both detectors and their radial drive mechanisms could be attached to the detector I ring gears 32 and 34. Accordingly, it is not intended to limit the invention except as provided by the appended claims.

What is claimed is:

1. An imaging system for acquiring imaging data generated by an object positioned about a lateral axis to form a SPECT image, said system comprising:

first and second gamma ray detectors;

a first pair of rings, oriented substantially perpendicular to and approximately centered on the lateral axis;

a second pair of rings, oriented substantially perpendicular to and centered approximately on said lateral axis means for coupling said first detector to said first pair of rings, with the first detector pointed toward the lateral axis and disposed between said rings;

means for coupling said second detector to said second pair of rings, with the second detector pointed toward said lateral axis and disposed between said rings; and means for independently rotating said first pair of rings to adjust the angular displacement, about the lateral axis, between said first and second detectors to a predetermined magnitude.

2. The imaging system of claim 1 further comprising:

means for rotating both said first and second pairs of rings to rotate the detectors about the lateral axis while maintaining a constant angular displacement therebetween.

3. The system of claim 1 wherein:

said means for coupling said first detector to said first pair of rings includes means for moving said first detector toward and away from the lateral axis; and said means for coupling said second detector to said second pair of rings includes means for moving said second detector toward and away from the lateral axis.

4. An imaging system for acquiring imaging data of an object positioned about a lateral axis to form a SPECT image, said system comprising:

first and second gamma ray detectors;

a first pair of rings, oriented substantially perpendicular to and approximately centered on the lateral axis;

a second pair of rings, oriented substantially perpendicular to and centered approximately on said lateral axis means for coupling said first detector to said first pair of rings, with the first detector pointed toward the lateral axis and disposed between said rings;

means for coupling said second detector to said second pair of rings, with the second detector pointed toward said lateral axis and disposed between said rings; and means for rotating said first and second pairs of rings to adjust the angular displacement, relative to the lateral axis, between said first and second detectors to a predetermined magnitude.

5. The system of claim 4 wherein:

said means for coupling said first detector to said first pair of rings includes means for moving said first detector toward and away from the lateral axis; and said means for coupling said second detector to said second pair of rings includes means for moving said second detector toward and away from the lateral axis.

6. The imaging system of claim 4 further comprising:

means for rotating both said first and second pairs of rings to rotate the detectors about the lateral axis while maintaining a constant angular displacement therebetween.

7. An imaging system for acquiring imaging data generated by an object positioned about a lateral axis, said system comprising:

first and second detectors, with the second detector being narrower than said first detector;

means for rotating said first and second detectors in a circular path approximately centered at said lateral axis and oriented perpendicularly to a lateral axis, with the angular displacement of the detectors fixed at a selected magnitude of about 90°;

means for moving said detectors toward or away from the lateral axis to decrease the distance between the detectors and the object to be imaged to improve resolution, where the narrower second detector facilitates minimizing the distance between the detectors and the body of a patient oriented along the lateral axis.

8. The system of claim 7 further comprising:

a table for supporting a patient;

means, coupled to said table to support said table and orient said table parallel to said lateral axis, for displacing the table, horizontally and vertically relative to the lateral axis, by a selected distance to increase the resolution of the imaging system.

9. An imaging system for acquiring imaging data generated by an object positioned about a lateral axis, said system comprising:

first and second detectors, with the second detector being narrower than said first detector; and means for rotating said first and second detectors in a circular path approximately centered at said lateral axis and oriented perpendicularly to a lateral axis, with the angular displacement of the detectors fixed at a selected magnitude of about 90°.

10. The system of claim 9 further comprising:

a table for supporting a patient;

means, coupled to said table to support said table and orient said table parallel to said lateral axis, for displacing the table, horizontally and vertically relative to the lateral axis, by a selected distance to increase the resolution of the imaging system.

11. An imaging system for acquiring imaging data generated by an object positioned about a lateral axis, said system comprising:

first and second detectors, with the second detector being narrower than the first detector;

means for rotating said first and second detectors in a circular path approximately centered at said lateral axis and oriented substantially perpendicular to a lateral axis with the angular displacement of the detectors fixed at a selected magnitude between 180° and about 90°; and extended collimators, coupled to said first and second detectors and pointed toward said lateral axis, for increasing the resolution of said imaging system.

* * * * *